United States Patent
Hirose et al.

(10) Patent No.: US 11,432,899 B2
(45) Date of Patent: Sep. 6, 2022

(54) MEDICAL OBSERVATION DEVICE AND MEDICAL OBSERVATION SYSTEM

(71) Applicants: SONY OLYMPUS MEDICAL SOLUTIONS INC., Hachioji (JP); SONY CORPORATION, Minato-ku (JP)

(72) Inventors: Kenji Hirose, Tokyo (JP); Hisayoshi Otaki, Tokyo (JP); Hiroki Sato, Kanagawa (JP); Shingo Mouri, Aichi (JP); Katsuhisa Hakoda, Kanagawa (JP); Daisuke Iseki, Tokyo (JP)

(73) Assignees: SONY OLYMPUS MEDICAL SOLUTIONS INC., Tokyo (JP); SONY CORPORATION, Tokyo (JP)

( * ) Notice: Subject to any disclaimer, the term of this patent is extended or adjusted under 35 U.S.C. 154(b) by 727 days.

(21) Appl. No.: 16/325,455

(22) PCT Filed: Jul. 19, 2017

(86) PCT No.: PCT/JP2017/026006
§ 371 (c)(1),
(2) Date: Feb. 14, 2019

(87) PCT Pub. No.: WO2018/055888
PCT Pub. Date: Mar. 29, 2018

(65) Prior Publication Data
US 2019/0167377 A1    Jun. 6, 2019

(30) Foreign Application Priority Data

Sep. 23, 2016 (JP) .............. JP2016-185074
Apr. 19, 2017 (JP) .............. JP2017-082460

(51) Int. Cl.
*A61B 90/25* (2016.01)
*G02B 21/00* (2006.01)
(Continued)

(52) U.S. Cl.
CPC .............. *A61B 90/25* (2016.02); *A61B 90/37* (2016.02); *A61B 90/50* (2016.02); *G02B 7/001* (2013.01);
(Continued)

(58) Field of Classification Search
CPC ......... A61B 90/25; A61B 90/37; A61B 90/50; A61B 90/20; A61B 46/10;
(Continued)

(56) References Cited

U.S. PATENT DOCUMENTS 7,436,927 B2   10/2008  Hempel
9,610,197 B2   4/2017   Wellhöfer
(Continued)

FOREIGN PATENT DOCUMENTS

CN      2623184 Y    7/2004
CN      101023890 A  8/2007
(Continued)

OTHER PUBLICATIONS

Office Action dated Jun. 3, 2021, in corresponding Chinese patent Application No. 201780056618.1, 16 pages.
(Continued)

*Primary Examiner* — Derek S. Chapel
*Assistant Examiner* — Adam W Booher
(74) *Attorney, Agent, or Firm* — Xsensus, LLP

(57) ABSTRACT

A medical observation device that includes a microscope that images a surgical site, a holding section that holds the microscope, a base section to which the holding section is connected, and an operation section that receives operating input, the operation section being provided at the base section, the holding section being configured as a balance arm provided with a counterweight, when the base section is viewed from an upper side of the medical observation device, the base section having a first area inside a movable (Continued)

range of the counterweight and a second area outside the movable range of the counterweight, the base end of the holding section being connected to the base section at a location in the first area, and the operation section being arranged at another location in the second area.

14 Claims, 7 Drawing Sheets

(51) Int. Cl.
| | | |
|---|---|---|
| G02B 21/24 | (2006.01) | |
| G02B 7/00 | (2021.01) | |
| A61B 90/50 | (2016.01) | |
| A61B 90/00 | (2016.01) | |
| A61B 46/10 | (2016.01) | |
| A61B 17/00 | (2006.01) | |

(52) U.S. Cl.
CPC ......... *G02B 21/0012* (2013.01); *G02B 21/24* (2013.01); *A61B 46/10* (2016.02); *A61B 2017/00199* (2013.01); *A61B 2017/00221* (2013.01); *A61B 2090/371* (2016.02); *A61B 2090/373* (2016.02); *A61B 2090/504* (2016.02); *A61B 2090/506* (2016.02); *A61B 2090/508* (2016.02)

(58) Field of Classification Search
CPC ........ A61B 2090/371; A61B 2090/373; A61B 2090/504; A61B 2090/506; A61B 2090/508; A61B 2090/5025; A61B 2017/00199; A61B 2017/00221; G02B 7/001; G02B 21/0012; G02B 21/24
See application file for complete search history.

(56) References Cited

U.S. PATENT DOCUMENTS

| | | | |
|---|---|---|---|
| 2001/0055062 A1 | 12/2001 | Shoida et al. | |
| 2005/0041282 A1 | 2/2005 | Rudolph et al. | |
| 2007/0165302 A1* | 7/2007 | Spetzler | G02B 21/0012 359/368 |
| 2007/0172102 A1 | 7/2007 | Hempel | |
| 2015/0018622 A1 | 1/2015 | Tesar et al. | |
| 2015/0085095 A1 | 3/2015 | Tesar | |
| 2016/0081755 A1 | 3/2016 | Wellhöfer | |
| 2016/0131880 A1 | 5/2016 | Kamata et al. | |
| 2016/0165222 A1* | 6/2016 | Yamaoka | A61B 90/20 348/51 |
| 2018/0256145 A1 | 9/2018 | Tesar et al. | |

FOREIGN PATENT DOCUMENTS

| | | | | |
|---|---|---|---|---|
| CN | 101579260 A | 11/2009 | | |
| CN | 102106718 A | 6/2011 | | |
| CN | 102469921 A | 5/2012 | | |
| CN | 104379096 A | 2/2015 | | |
| CN | 104661612 A | 5/2015 | | |
| EP | 2999414 A1 * | 3/2016 | ............... | A61B 1/05 |
| JP | H09182759 A | 7/1997 | | |
| JP | 10-33554 A | 2/1998 | | |
| JP | 2005-43458 A | 2/2005 | | |
| JP | 2005-143970 A | 6/2005 | | |
| JP | 2005312529 A | 11/2005 | | |
| JP | 2014113237 A | 6/2014 | | |
| JP | 2015126288 A | 7/2015 | | |
| WO | 03/002011 A1 | 1/2003 | | |
| WO | WO 2015/042460 A9 | 3/2015 | | |
| WO | WO 2015/137040 A1 | 9/2015 | | |

OTHER PUBLICATIONS

International Search Report dated Oct. 10, 2017, in PCT/JP2017/026006 filed on Jul. 19, 2017.
"OPMI PENTERO 900", catalogue, Carl Zeiss Meditec AG [online], 2011, [retrieval date Sep. 9, 2017], <URL: https://applications.zeiss.com/C1257BB3003850AB/0/9C42EDAF187691B8C1257A29005873AC/$FILE/PENTER0900_BRCH_US_30_010_900III_sec.pdf>, total 7 pages.
"Leica M530 OH6" catalogue, Leica Microsystems, 2015, total 16 pages.
Extended European Search Report dated Aug. 1, 2019 in European Application No. 17852669.5-1020.

* cited by examiner

MEDICAL OBSERVATION DEVICE AND MEDICAL OBSERVATION SYSTEM

TECHNICAL FIELD

The present disclosure relates to a medical observation device and a medical observation system.

BACKGROUND ART

For example, in surgery (so-called microsurgery) in which microscopic regions such as neurosurgery become a target, observation devices for enlarged stereoscopic observation of the surgical site are used. An observation device includes a microscope section held by an arm section (holding section) (for example, Non-Patent Literatures 1 and 2).

The microscope section of the observation device described in Non-Patent Literatures 1 and 2 is an optical type, and a surgeon observes a surgical site directly by looking into the microscope section from an eyepiece section disposed in the microscope section. Hereinafter, an observation device equipped with a microscope section of an optical type is also referred to as an optical type observation device.

In such an optical type microscope section, an eyepiece section for an assistant may further be provided in addition to the eyepiece section for a surgeon as described above. Also, a variable magnification mechanism and variable focal point mechanism may also be provided inside the microscope section. Therefore, the optical microscope section tends to be relatively large in size and weight.

Meanwhile, an operation of causing the position of the microscope section to move in order to change a site to be observed may happen during surgery. Since a significantly small range is observed in an enlarged manner at this time, it becomes necessary to cause the position of the microscope section to move by a minute amount. Therefore, in order to make it possible to move the relatively large microscope section with small force, the holding section of the optical type observation device is configured as a balance arm that employs a parallel link mechanism in many cases. The balance arm forms the holding section by providing a counterweight on a base end side such that moment of the entire holding section is balanced. In the optical type observation device, the counterweight also tends to be large in size due to the large microscope section.

Further, in the optical type observation device, the holding section that holds the microscope section also tends to be large in size due to the large microscope section. Therefore, a style in which a surgeon comes under the holding section and performs observation (hereinafter, referred to as an overhead style) is a mainstream of the optical type observation device. Therefore, in the optical type observation device, the holding section is formed to have a sufficient length to enable observation in such an overhead style, and the holding section also tends to be relatively large in size and weight. If the holding section is formed to have a large size in this manner, the counterweight tends to be further larger.

In this manner, the counterweight also tends to be relatively large in the optical observation device due to the relatively large microscope section and holding section. If the counterweight is large, the movable range of the counterweight caused by movement of the holding section also increases.

Here, a control section that is formed with a control substrate or the like and an operation section such as a touch panel for receiving operating input for various kinds of setting during observation, and the like are provided in the observation device. If it is attempted to provide these configurations separately from the holding section, it is necessary that these configurations be arranged outside the movable range of the counterweight in order not to prevent movement of the holding section. In this case, the entire size of the observation device increases, and the observation device occupies a space in an operating room, which is unfavorable.

Thus, in order to further reduce the size of the observation device, a control section and an operation section are provided as a part of a holding section in observation devices described in Non-Patent Literatures 1 and 2. Specifically, the observation devices have a configuration in which a base end of a holding section is connected to an upper surface of a base section mounted on a floor surface, and a rotational axis section that can rotate about a rotational axis parallel to the vertical direction relative to the base section is provided at the base end of the holding section connected to the upper surface of the base section. In Addition, the control section and the operation section are integrally formed with a link that is connected to the tip end side of the rotational axis section.

According to such a configuration, since the counterweight, the control section, and the operation section rotate together with the rotation about the aforementioned rotational axis, a situation in which the control section and operation section interfere with the movable range of the counterweight does not occur. Therefore, it is possible to form a relatively small holding section. Also, the operation section is provided on the side of a side surface of the counterweight in the observation device. Therefore, an operator who performs various kinds of operating input via the operation section is located on the side of the side surface of the counterweight, it is possible to avoid a situation in which the operator prevents movement of the counterweight in the front-back direction (the direction in which the holding section extend when viewed from the base section), that is, a situation in which the operator prevents movement of the holding section in the front-back direction.

CITATION LIST

Non-Patent Literature

Non-Patent Literature 1: "Leica M530 OH6" catalogue, Leica Microsystems, 2015
Non-Patent Literature 2: "OPMI PENTERO 900" catalogue, Carl Zeiss Meditec, 2011

SUMMARY OF INVENTION

Technical Problem

Here, in recent years, in observation devices, those that are equipped with an image sensor and are equipped with an electronic imaging type microscope section capable of imaging a surgical site electronically, have been developed. In the observation device equipped with the microscope section of the electronic imaging type (hereinafter, also referred to as an observation device of an electronic imaging type), an image of a surgical site photographed by the microscope section is displayed on a display device installed in an operating room, and a surgeon performs surgery while observing the surgical site displayed on the display device.

The electronic imaging type microscope section can be formed to a small size and a light weight as compared with the optical type microscope section for reasons such as because the eyepiece section is not provided and because it is not necessary to provide a complicated optical system inside the microscope section. Since the microscope section is reduced in size, it is also possible to reduce the size of the holding section and to reduce the size of the counterweight. In this manner, the electronic imaging type observation device has a feature that it is possible to form the optical type observation device to a small size.

Therefore, according to the electronic imaging type observation device, it is possible to reduce the size of the entire device even if the control section and the operation section are not configured as a part of the holding section and thereby to more freely arrange these configurations in the device. In other words, there is a probability that appropriate arrangement of the control section and the operation section different from that in the optical type observation device may be present in the electronic imaging type observation device. In particular, there is a probability that the arrangement of the operation section affects convenience of the operator who performs various kinds of operating input via the operation section, it is important to appropriately arrange the operation section in order to realize smooth surgery.

Thus, the present disclosure proposes a novel and improved medical observation device and a medical observation system that enable more smooth surgery.

Solution to Problem

According to the present disclosure, there is provided a medical observation device including: a microscope section that images a surgical site; a holding section that holds the microscope section on a tip end side; a base section to which a base end of the holding section is connected; and an operation section that is provided at the base section for performing various kinds of operating input.

In addition, according to the present disclosure, there is provided a medical observation system including: a medical observation device that includes a microscope section that images a surgical site, a holding section that holds the microscope section on a tip end side, a base section to which a base end of the holding section is connected, and an operation section that is provided at the base section for performing various kinds of operating input; and a display device that displays an image captured by the medical observation device.

According to the present disclosure, the operation section for performing various kinds of operating input is provided at the base section rather than the holding section in the observation device. Therefore, it is possible to change the position and the orientation of the operation section while fixing the position and the attitude of the microscope section held on the tip end side of the holding section. Therefore, it is possible to appropriately adjust the position of the operator who performs various kinds of operating input via the operation section during surgery and to thereby more smoothly perform surgery.

Advantageous Effects of Invention

According to the present disclosure, it is possible to more smoothly perform surgery as described above. Note that the effects described above are not necessarily limitative. With or in the place of the above effects, there may be achieved any one of the effects described in this specification or other effects that may be grasped from this specification.

DESCRIPTION OF EMBODIMENTS

Figure 1:
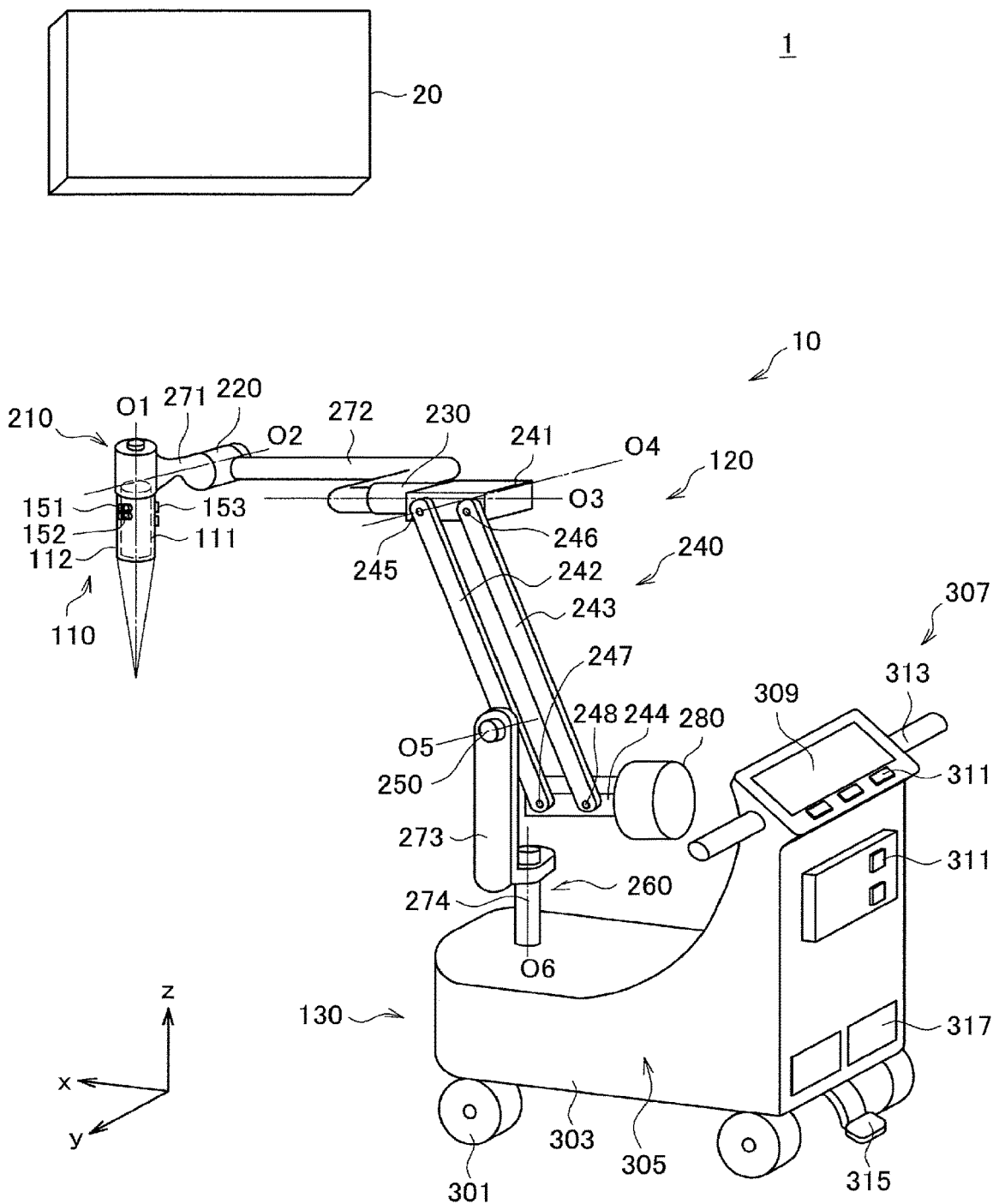
FIG. 1 is a diagram schematically illustrating configuration examples of an observation system according to the embodiment and an observation device according to a first embodiment.

Hereinafter, (a) preferred embodiment(s) of the present disclosure will be described in detail with reference to the appended drawings. In this specification and the appended drawings, structural elements that have substantially the same function and constitution are denoted with the same reference numerals, and repeated explanation of these structural elements is omitted.

Note that description will be given in the following order.
1. Configurations of observation system and observation device
2. Advantages of observation device
3. Operations during use 4 Other configuration examples of observation device
5. Supplement 1. Configurations of Observation System and Observation Device Referring to FIG. 1, configurations of an observation system and an observation device according to an embodiment of the present disclosure will be described. FIG. 1 is a diagram schematically illustrating a configuration example of an observation system according to the embodiment and an observation device 10 according to a first embodiment.

Referring to FIG. 1, the observation system 1 according to the present embodiment includes an observation device 10 that is an observation device of an electronic imaging type for performing enlarged observation of a patient's surgical site, and a display device 20 that displays the image of the surgical site photographed by the observation device 10. The observation system 1 is a medical observation system for observing an observation target portion (surgical target portion (surgical site) or inspection target portion) being a part of a patient's body at the time of performing medical practices, such as surgery and inspection. Further, the observation device 10 is a medical observation device for observing the observation target portion. At the time of surgery or at the time of inspection, a surgeon observes an observation target portion via an image photographed by the observation device 10 and displayed on the display device 20, and, performs various kinds of treatments for the observation target portion if needed. Hereinafter, description is given for a case of performing surgery by using the observation system 1, and its observation target portion is also referred to as a surgical site.

(Display Device)

Under the control of the control section 305 provided in the observation device 10 described later, the display device 20 displays the image of the patient's surgical site photographed by the observation device 10. The display device 20 is installed in a location visible to the surgeon in an operating room, such as on a wall of the operating room, for example. The type of the display device 20 is not particularly limited, and any of various publicly known types of display devices may be used as the display device 20, such as a cathode ray tube (CRT) display device, a liquid crystal display device, a plasma display device, or an electroluminescence (EL) display device. Additionally, the display device 20 is not necessarily required to be installed inside the operating room, and may also be mounted onboard a device used by being worn on the surgeon's body, such as a head-mounted display (HMD) or an eyeglasses-type wearable device.

Note that, as will be described later, in a case in which an imaging section 111 of the microscope section 110 of the observation device 10 is configured as a stereo camera, or such that high-resolution imaging is possible, a display device 20 capable of 3D display or capable of displaying an image with high resolution may be used accordingly.

(Observation Device)

The observation device 10 is equipped with a microscope section 110 for performing enlarged observation of the patient's surgical site, a holding section 120 that holds the microscope section 110, and a base section 130 to which a base end of the holding section 120 is connected and which supports the microscope section 110 and the holding section 120.

Note that in the following description, the direction that is vertical to a floor surface on which the observation device 10 is mounted will be defined as a z axis direction. The z axis direction will also be referred to as an upper-lower direction. Also, the direction, which is perpendicular to the z axis direction, in which the holding section 120 extends from the base section 130 will be defined as an x axis direction. The x axis direction will also be referred to as a front-back direction. Also, the direction that is perpendicular to both the x axis direction and the z axis direction will be defined as a y axis direction. The y axis direction will be also referred to as a left-right direction. Also, the plane that is parallel to the x-y plane will also be referred to as a horizontal plane.

(Microscope Section)

The microscope section 110 is an electronic imaging type microscope section. In the example illustrated in the drawing, an optical axis direction of the microscope section 110 substantially coincides with the z axis direction. The microscope section 110 is formed with a barrel section 112 that has a substantially cylindrical shape and an imaging section 111 that is provided in the barrel section 112.

The aperture on the bottom end of the barrel section 112 is provided with a cover glass for protecting the imaging section 111. A light source is also provided inside the barrel section 112, and during image photograph, the subject is irradiated with illuminating light radiating from the light source through the cover glass. Of this illuminating light, the light reflecting back from the subject (observation light) is incident on the imaging section 111 via the cover glass.

The imaging section 111 is formed with an imaging element and an optical system that collects observation light at the imaging element. The optical system includes various lenses such as an object lens, a zoom lens, and a focus lens and an optical element such as a mirror, and optical properties and arrangement of the respective elements are adjusted such that the observation light is collected on a light receiving surface of the imaging element. Note that for the zoom lens and the focus lens, a drive mechanism for moving the positions thereof on an optical axis can be provided to adjust the magnitude and the focal distance. A signal (image signal) related to an image of an object is acquired by the imaging element by the observation light being incident on the imaging element and being subject to photoelectric conversion. The image signal acquired by the imaging section 111 is transmitted to the control section 305, which will be described later.

Note that, for the imaging section 111, it is sufficient to apply a configuration used in any of various publicly known types of electronic imaging microscope sections, and for this reason a detailed description thereof will be reduced or omitted herein. For example, any of various publicly known types of image sensors may be applied as the image sensor of the imaging section 111, such as a charge-coupled device (CCD) sensor or a complementary metal-oxide-semiconductor (CMOS) sensor. Additionally, the imaging section 111 may be capable of 3D display to also be configured as a stereo camera equipped with a pair of image sensors. Alternatively, the imaging section 111 may be configured to be able to capture images with high resolution such as 4K or 8K, for example. It is possible to improve visibility of the surgeon who views an image captured by the imaging section 111 by the imaging section 111 performing image capturing compatible with 3D display or performing image capturing with high resolution. Also, any of various publicly known types of configurations may be applied to the optical system of the imaging section 111. Furthermore, any of various types of functions typically provided in electronic imaging microscope sections, such as an autofocus (AF) function and an optical zoom function, may be provided onboard the imaging section 111.

The microscope section 110 is provided with various types of switches for controlling the operation of the microscope section 110. For example, the microscope section 110 is provided with a zoom switch 151 (zoom SW 151) and a focus switch 152 (focus SW 152) for adjusting the image photograph parameters of the microscope section 110, as well as an operation mode changing switch 153 (operation mode changing SW 153) for toggling the operating mode of the holding section 120.

The surgeon, by operating the zoom SW 151 and the focus SW 152, is able to adjust the magnification and the focal length of the imaging section 111, respectively. Also, by operating the operation mode changing SW 153, the surgeon is able to toggle the operating mode of the holding section 120 between a locked mode and a free mode.

Herein, the locked mode is an operating mode in which the position and the attitude of the microscope section 110 are locked by using a brake to restrain rotation about each rotation axis in the holding section 120. The free mode is an operating mode in which the brake is released, thereby allowing free rotation about each rotation axis in the holding section 120. For example, in the free mode, it is possible to adjust the position and the attitude of the microscope section 110 with direct operations by the surgeon. Herein, direct operations mean operations in which the surgeon grips the microscope section 110 with his or her hand, for example, and directly moves the microscope section 110. For example, the operating mode of the holding section 120 becomes the free mode while the surgeon is pressing the operation mode changing SW 153, and the operating mode of the holding section 120 becomes the locked mode while the surgeon releases his or her hand from the operation mode changing SW 153.

Note that these switches are not necessarily required to be provided on the microscope section 110. In the present embodiment, it is sufficient for the observation device 10 to be provided with a mechanism for accepting operating input having functions similar to these switches, and the specific configuration of such a mechanism is not limited. For example, these switches may also be provided on another section of the observation device 10. Specifically, an operation section 307 may include functions corresponding to these switches. Alternatively, for example, an input device such as a remote control, a foot switch or the like may be used, and commands corresponding to these switches may be input into the observation device 10 remotely.

Also, although the barrel section 112 of the microscope section 110 is illustrated as a simple cylindrically-shaped member in FIG. 1 for the sake of simplicity, the barrel section 112 may also be provided with a grip section gripped by the surgeon. Such a grip section may be realized by having a constitution such as a handle to be gripped by the surgeon be formed around the outer circumference of the barrel section 112. Alternatively, such a grip section may be realized by having the shape of the barrel section 112 be formed into a shape that is gripped easily by the surgeon. For example, as described above, when in the free mode, operations of moving the microscope section 110 with the surgeon gripping the barrel section 112 directly in hand may be anticipated. At this point, since the surgeon performs an operation of moving the microscope section 110 while pressing the operation mode changing SW 153, the shape of the barrel section 112 and the placement of the operation mode changing SW 153 may be determined appropriately with consideration for operability by the surgeon while in the free mode. In addition, the placement of the zoom SW 151 and the focus SW 152 may be determined appropriately with similar consideration for operability by the surgeon.

(Supporting Section)

The holding section 120 moves the microscope section 110 three dimensionally, and, supports the microscope section 110 at the position and attitude fixedly after the moving. In the present embodiment, the holding section 120 is constituted as a balance arm having six degrees of freedom. However, the present embodiment should not be limited to this example, and, the holding section 120 may be constituted so as to be able to move the microscope section 110 appropriately in accordance with an intended use, and, may be constituted so as to have other different number of degrees of freedom.

The holding section 120 is provided with six rotational axes (the first axis O1, the second axis O2, the third axis O3, the fourth axis O4, the fifth axis O5 and the sixth axis O6) corresponding to the six degrees of freedom. Hereinafter, for convenience for description, it is assumed that the members that constitute respective rotational axes are collectively referred to as a rotational axis section. For example, the rotational axis section may include a bearing, a shaft inserted rotatably through the bearing, a brake to regulate the rotation on the rotational axis, and so on. A later-mentioned parallelogram link mechanism 240 can be deemed also as one of the rotational axis sections.

The holding section 120 includes a first rotational axis section 210, a second rotational axis section 220, a third rotational axis section 230, a fourth rotational axis section 240, a fifth rotational axis section 250, and a sixth rotational axis section 260 corresponding to the respective rotation axes; a first arm section 271, a second arm section 272, a third arm section 273, and a fourth arm section 274 that are connected rotatably to each other by these first rotational axis section 210 to sixth rotational axis section 260; and a counterweight 280 for taking balance of moment of the microscope section 110 and the holding section 120 as a whole. In this connection, the fourth rotational axis section 240 corresponds to the parallelogram link mechanism 240.

Note that in the description below, when describing the constitution of the holding section 120, the side on which the microscope section 110 is provided will also be referred to as the tip end side or the tip end portion or the like, and the side near the base section 130 will also be referred to as the base end side or the base end portion or the like.

The first rotational axis section 210 has a generally cylindrical shape, and is connected to the base end portion of the barrel section 112 of the microscope section 110 such that the central axis of the first joint section 210 is substantially coincident with the central axis of the barrel section 112 of the microscope section 110. The first rotational axis section 210 rotatably supports the microscope section 110, with the direction substantially coincident with the optical axis of the microscope section 110 as the rotational axis direction (the direction of the first axis O1). In the example illustrated in FIG. 1, the first axis O1 is provided as a rotational axis that is substantially parallel to a z-axis. The orientation of the image photographed by the microscope section 110 is adjusted by rotating the microscope section 110 about the first axis O1 by the first rotational axis section 210.

Note that in the illustrated example, a portion of the imaging section 111 of the microscope section 110 is housed inside a cylindrical case that forms the first rotational axis section 210. That is, the microscope section 110 and the first rotational axis section 210 are configured as an integrated member. However, the present embodiment is not limited to this example. The first rotational axis section 210 and the microscope section 110 may also be configured as separate members.

A tip end of the first arm section 271 that extends in a direction substantially perpendicular to the first axis O1 is connected to the first rotational axis section 210. Also, the second rotational axis section 220 that rotatably supports the first arm section 271, with a direction substantially parallel to the direction in which the first arm section 271 extends as the rotational axis direction (the direction of the second axis O2), is provided on a base end of the first arm section 271. The second axis O2 is a rotational axis that is substantially perpendicular to the first axis O1, and is provided as a rotational axis that is substantially parallel to the y-axis in the example illustrated in FIG. 1. The position in the x-axis direction of the microscope section 110 is adjusted by rotating the microscope section 110 and the first arm section 271, with the second axis O2 as the rotational axis, by the second rotational axis section 220.

To the second rotational axis section 220, connected is the tip of the second arm section 272 that extends in a direction approximately vertical mutually to the first axis O1 and the second axis O2. Moreover, a base end side of the second arm section 272 is bent in an almost L form, and on a position corresponding to a folded short side, disposed is the third rotational axis section 230 that makes a direction almost parallel to the stretching direction of a portion corresponding to the long side of the second arm section 272 to the rotational axis direction (the third axis O3 direction) and supports the second arm section 272 rotatably. The third axis O3 is a rotational axis almost vertical to the first axis O1 and the second axis O2, and, in an example shown in FIG. 1, is disposed as a rotational axis almost parallel to the x axis. With the third rotational axis section 230, on the third axis O3 serving as a rotational axis, the microscope section 110, the first arm section 271, and the second arm section 272 are made to rotate, whereby the position, in the y axis direction, of the microscope section 110 will be adjusted.

In this way, the holding section 120 is configured such that the attitude of the microscope section 110 is controlled by controlling the rotation about both the second axis O2 and the third axis O3. That is, the second rotational axis section 220 and the third rotational axis section 230 can be rotational axis sections that define the attitude of the microscope section 110.

To the base end side of the third rotational axis section 230, the tip of the upper side of the parallelogram link mechanism 240 is connected. The parallelogram link mechanism 240 includes four arms (arms 241, 242, 243, and 244) arranged in the form of a parallelogram, and four joint sections (joint sections 245, 246, 247, and 248) disposed at the respective positions corresponding to the almost vertexes of the parallelogram.

The tip end of the arm 241 that extends in a direction substantially parallel to the third axis O3 is connected to the third rotational axis section 230. The joint section 245 is provided near the tip end of the arm 241, and the joint section 246 is provided near the base end of the arm 241. The tip ends of the arms 242 and 243 are connected to the joint sections 245 and 246, respectively, in a manner that enables the tip ends of the arms 242 and 243 to rotate about rotational axes (the fourth axis O4) that are substantially perpendicular to the direction in which the arm 241 extends, and substantially parallel to each other. Moreover, the joint sections 247 and 248 are provided on base ends of the arms 242 and 243, respectively. A tip end and a base end of the arm 244 are connected to these joint sections 247 and 248, respectively, in a manner able to rotate about the fourth axis O4 and substantially parallel to the arm 241.

In this way, the four joint sections that form the parallelogram link mechanism 240 have rotational axes (the fourth axis O4) in substantially the same direction that are substantially parallel to each other, and operate in conjunction with each other about the fourth axis O4. In the example illustrated in FIG. 1, the fourth axis O4 is provided as a rotational axis that is substantially parallel to the y-axis. That is, the parallelogram link mechanism 240 is configured to have a plurality of joint sections that are arranged in different positions from each other, and that rotate in conjunction with each other on rotational axes that are in the same direction, such that the parallelogram link mechanism 240 behaves as a transmission mechanism that transmits operation at one end to the other end. By disposing the parallelogram link mechanism 240, the movement of the constitutions (i.e., the microscope section 110, the first rotational axis section 210, the second rotational axis section 220, the third rotational axis section 230, the first arm section 271, and the second arm section 272) on the tip end side than the parallelogram link mechanism 240, is transmitted to the base end side of the parallelogram link mechanism 240.

The fifth rotational axis section 250 that rotatably supports the parallelogram link mechanism 240, with a direction perpendicular to the direction in which the arm 242 extends as the rotational axis direction (the direction of the fifth axis O5), is provided on a portion a predetermined distance away from the base end of the arm 242. The fifth axis O5 is a rotational axis that is substantially parallel to the fourth axis O4, and is provided as a rotational axis that is substantially parallel to the y-axis in the example illustrated in FIG. 1. To the fifth rotational axis section 250, the tip end of the third arm section 273 being stretched in the z axis direction is connected, and the microscope section 110, the first arm section 271, the second arm section 272, and the parallelogram link mechanism 240 are constituted to be rotatable relative to the third arm section 273 on the fifth axis O5 serving as a rotational axis via the fifth rotational axis section 250.

The third arm section 273 has a form of an almost L shape, and its base end side is bent so as to become almost parallel to a floor. To a surface, almost parallel to the floor, of the third arm section 273, connected is the sixth rotational axis section 260 on which the third arm section 273 is rotatable around a rotational axis (the sixth axis O6) orthogonal to the fifth axis O5. In the example shown in FIG. 1, the sixth axis O6 is disposed as a rotational axis almost parallel to the z axis.

In the example shown in the illustration, the sixth rotational axis section 260 is constituted integrally with the fourth arm section 274 extending in the vertical direction. That is, the tip end of the fourth arm section 274 is connected to the surface, almost parallel to the floor, of the base end of the third arm section 273. Moreover, the base end of the fourth arm section 274 is connected to the upper surface of the base section 130. With this constitution, the microscope section 110, the first arm section 271, the second arm section 272, the parallelogram link mechanism 240, and the third arm section 273 rotates relative to the base section 130 on the sixth O6 serving as a rotational axis via the sixth rotational axis section 260.

The arm 244 that forms the lower side of the parallelogram link mechanism 240 is formed longer than the arm 241 that forms the upper side of the parallelogram link mechanism 240, and the end of the arm 242 that is positioned diagonally opposite the portion of the parallelogram link mechanism 240 to which the third rotational axis section 230 is connected extends to the outside of the parallelogram link mechanism 240. The counterweight 280 is provided on the extending end of the arm 244. The mass and placement position of the counterweight 280 are adjusted such that the rotation moment generated about the fourth axis O4 and the rotation moment generated about the fifth axis O5 are able to cancel each other out by the mass of the constitutions (i.e., the microscope section 110, the first rotational axis section 210, the second rotational axis section 220, the third rotational axis section 230, the first arm section 271, the second arm section 272, and the parallelogram link mechanism 240) that are arranged to the tip end side of the counterweight 280 itself.

Also, the placement position of the fifth rotational axis section 250 is adjusted such that the center of gravity of each of the constitutions arranged to the tip end side of the fifth rotational axis section 250 is positioned on the fifth axis O5. Moreover, the placement position of the sixth rotational axis section 260 is adjusted such that the center of gravity of each of the constitutions arranged to the tip end side of the sixth rotational axis section 260 is positioned on the sixth axis O6.

By having the mass and placement position of the counterweight 280, the placement position of the fifth rotational axis section 250, and the placement position of the sixth rotational axis section 260 configured in this way, the holding section 120 can be configured as a balance arm in which the moments of the microscope section 110 and the holding section 120 are balanced on the whole. By constituting the holding section 120 as a balance arm, in the case where a surgeon intends to move the microscope section 110 by a direct operation, it becomes possible to move the microscope section 110 with a smaller external force as if it was under weightlessness. Therefore, the operativity of the surgeon can be improved.

The first rotational axis section 210 to the sixth rotational axis section 260 of the holding section 120 are provided with respective brakes that regulate the rotations on the first rotational axis section 210 to the sixth rotational axis section 260. In this connection, in the parallelogram link mechanism 240, the four joint sections (joint sections 245 to 248) rotate mutually in conjunction with each other. Accordingly, it is sufficient if a brake for the parallelogram link mechanism 240 is disposed for at least any of these four joint sections. The driving of these brakes is controlled by the control section 305 described later. By releasing these brakes all at once under the control from the control section 305, the operational mode of the holding section 120 shifts to a free mode. Moreover, similarly, under the control from the control section 305, by actuating these brakes all at once, the operational mode of the holding section 120 shifts to a fixed mode.

In this connection, as the brake disposed in the first rotational axis section 210 to the sixth rotational axis section 260, various kinds of brakes used for a general balance arm may be applied, and its concrete mechanism is not limited. For example, these brakes may be those driven mechanically, or may be electromagnetic brakes driven electrically.

(Base Section)

The base section 130 supports the microscope section 110 and the holding section 120. The base section 130 has a case body 303 and a plurality of casters 301 that are provided on the lower surface of the case body 303. A base end of the holding section 120 is connected to the upper surface of the case body 303. Also, the observation device 10 is formed such that the observation device 10 is in contact with the floor surface via the casters 301 and can move along the floor surface due to the casters 301.

As illustrated in FIG. 1, for example, the base end of the holding section 120 is connected between the casters 301 provided on the front side (on the positive side of the x axis illustrated in FIG. 1) of the case body 303 and the casters 301 provided on the rear side (on the negative side of the x axis illustrated in FIG. 1) of the case body 303 on the upper surface of the case body 303. That is, the casters 301 capable of moving along the contact surface are provided on the front side beyond the position to which the base end of the holding section 120 is connected in the horizontal plane of the base section 130 and on the rear side beyond the position to which the base end of the holding section 120 is connected in the horizontal plane of the base section 130, respectively, in the base section 130.

The case body 303 has a portion with a substantially rectangular shape (substantially rectangular parallelpiped shape) and a portion with a wall shape that is provided to protrude upward from a position corresponding to one side of the upper surface of the portion with the substantially rectangular shape (in the example illustrated in the drawings, the position corresponding to the side located on the negative side of the x axis (that is, the rear side) that is a long-side direction in the horizontal plane). The base end of the holding section 120, that is, the base ends of the sixth rotational axis section 260 and the fourth arm section 274 are connected to the upper surface of the portion with the substantially rectangular shape of the case body 303.

In the case body 303, the control section 305 that controls operations of the observation system 1 and the observation device 10 is provided. Since the case body 303 has a portion with the wall shape on the rear side (the negative side of the x axis illustrated in FIG. 1) of the case body 303, it is possible to arrange a larger number of parts on the rear side of the case body 303 than on the front side (the positive side of the x axis illustrated in FIG. 1) of the case body 303 in the case body 303. In addition, the operation section 307 that receives various kinds of operating input performed on the observation system 1 and the observation device 10 is provided in the wall surface (that is, the wall surface located on the negative side of the x axis in the portion with the wall shape) that faces the outside of the portion with the wall shape of the case body 303. Note that in a case in which a simple description "operator" is used in the following description, this means a member of medical staff who performs various kinds of operating input via the operation section 307. As described above, the observation device 10 according to the embodiment is an electronic imaging type observation device and can be a smaller device than the optical type observation devices as described in Non-Patent Literature 1 and 2, for example. Therefore, it is possible to keep the device to a small size even if the control section 305 and the operation section 307 are provided in the base section 130 in this manner. Also, it is possible to reduce the size of the device and to improve usability for the operator by forming the base section 130 with the case body 303 that has the portion with the wall shape and providing the operation section 307 on the wall surface that faces the outside of the portion with the wall shape of the case body 303 as illustrated in FIG. 1, for example.

Figure 2:
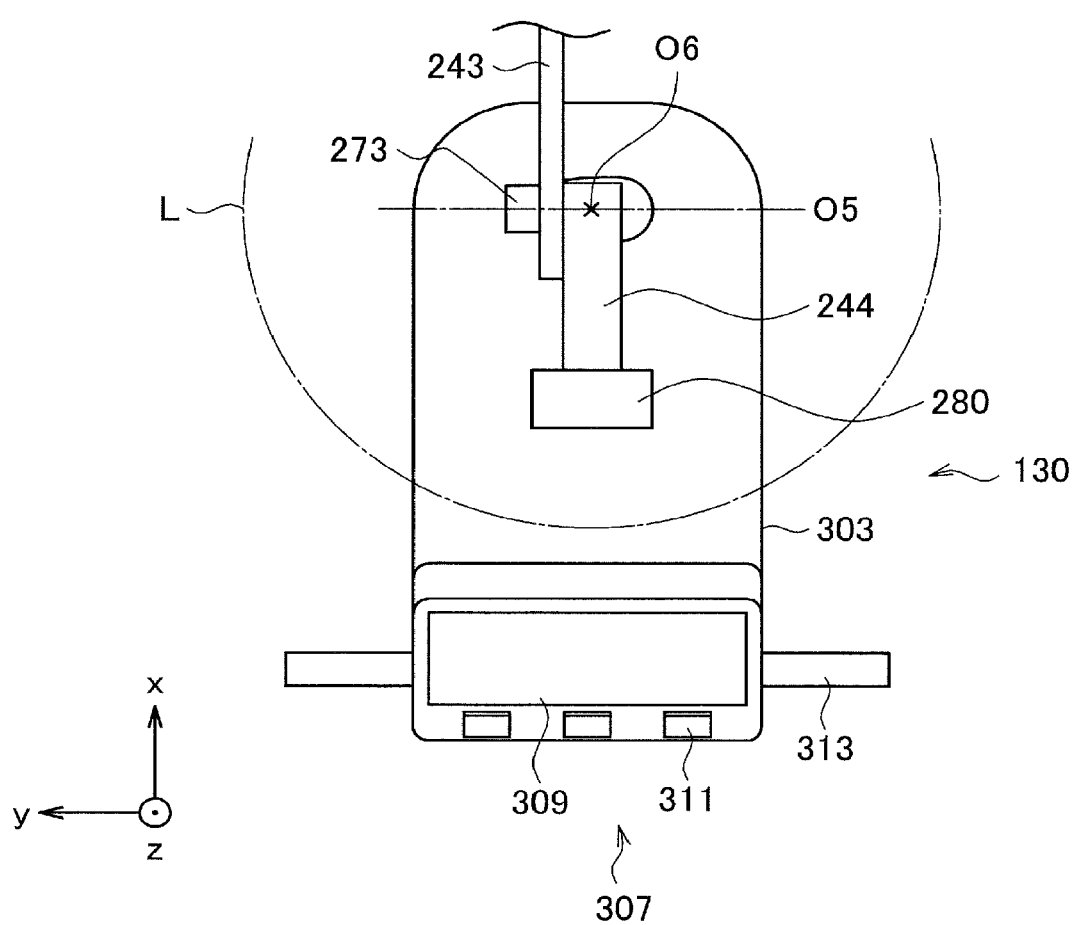
FIG. 2 is a diagram for describing arrangement of an operation section.

As illustrated in FIG. 2, the operation section 307 (that is, the portion with the wall shape of the case body 303 at which the operation section 307 is provided) is provided at a position at which the operation section 307 does not interfere with the movable range of the counterweight 280. FIG. 2 is a diagram for describing the arrangement of the operation section 307. FIG. 2 schematically illustrates a state in which the vicinity of the base section 130 of the observation device 10 is viewed from the upper side. Also, the movable range of the counterweight 280 is represented by the single dotted-dashed line to which the symbol L applies. As illustrated in the drawings, the portion with the wall shape does not prevent operations of the holding section 120 due to the portion with the wall shape of the case body 303 being arranged outside the movable range of the counterweight 280. In addition, since the operation section 307 is provided in the wall surface that faces the outside of the portion with the wall shape of the case body 303, the operator is positioned outwards from the portion with the wall shape when the operator performs operating input on the operation section 307. Therefore, the operator does not prevent operations of the holding section 120.

Here, the base end of the holding section is connected to an approximate center in the horizontal plane of the upper surface of the base section in the optical type observation devices as described in Non-Patent Literatures 1 and 2, for example. Meanwhile, according to the embodiment, the base end of the holding section 120 is connected to a position deviating from the approximate center in the horizontal plane of the upper surface of the case body 303 toward the front side by a predetermined distance. That is, the sixth axis O6 is at a position deviating from the approximate center in the horizontal plane of the upper surface of the case body 303 toward the front side. Here, the approximate center in the horizontal plane of the upper surface of the case body 303 according to the embodiment refers to "a center position (or a center of gravity position; the same is true for the following description) in the horizontal plane of the upper surface of the case body 303" or "a position at a distance therefrom that is sufficiently small and can be regarded as being the same as the center position", for example. Also, the portion with the wall shape at which the operation section 307 is provided is provided on the rear side of the case body 303, that is, on the side opposite to the side to which the base end of the holding section 120 is connected when viewed from the approximate center in the horizontal plane. As described above, the holding section 120 and the portion with the wall shape at which the operation section 307 is provided are provided on mutually opposite sides with the approximate center in the horizontal plane interposed therebetween in the upper surface of the case body 303. In this manner, the holding section 120 and the operation section 307 are arranged relatively away from each other. Therefore, it is possible to keep the case body 303, that is, the base section 130 in a relatively small size even if the operation section 307 is provided outside the movable range of the counterweight 280 as described above. Note that it is needless to say that the base end of the holding section 120 may be connected to the approximate center in the horizontal plane of the upper surface of the case body 303 in the observation device according to the embodiment.

In addition, the case body 303 is formed to have a long-side direction and a short-side direction in the horizontal plane as illustrated in FIG. 2, and the long-side direction corresponds to the front-back direction. That is, the base end of the holding section 120 is connected to a position deviating from the approximate center in the horizontal plane of the case body 303 toward one end side in the long-side direction by a predetermined distance. Also, the portion with the wall shape at which the operation section 307 is provided is formed on the other end side in the long-side direction. According to such a configuration, it is possible to further increase the distance between the holding section 120 and the operation section 307 and to thereby keep the base section 130 further in a smaller size while arranging the operation section 307 outside the movable range of the counterweight 280.

Figure 3:
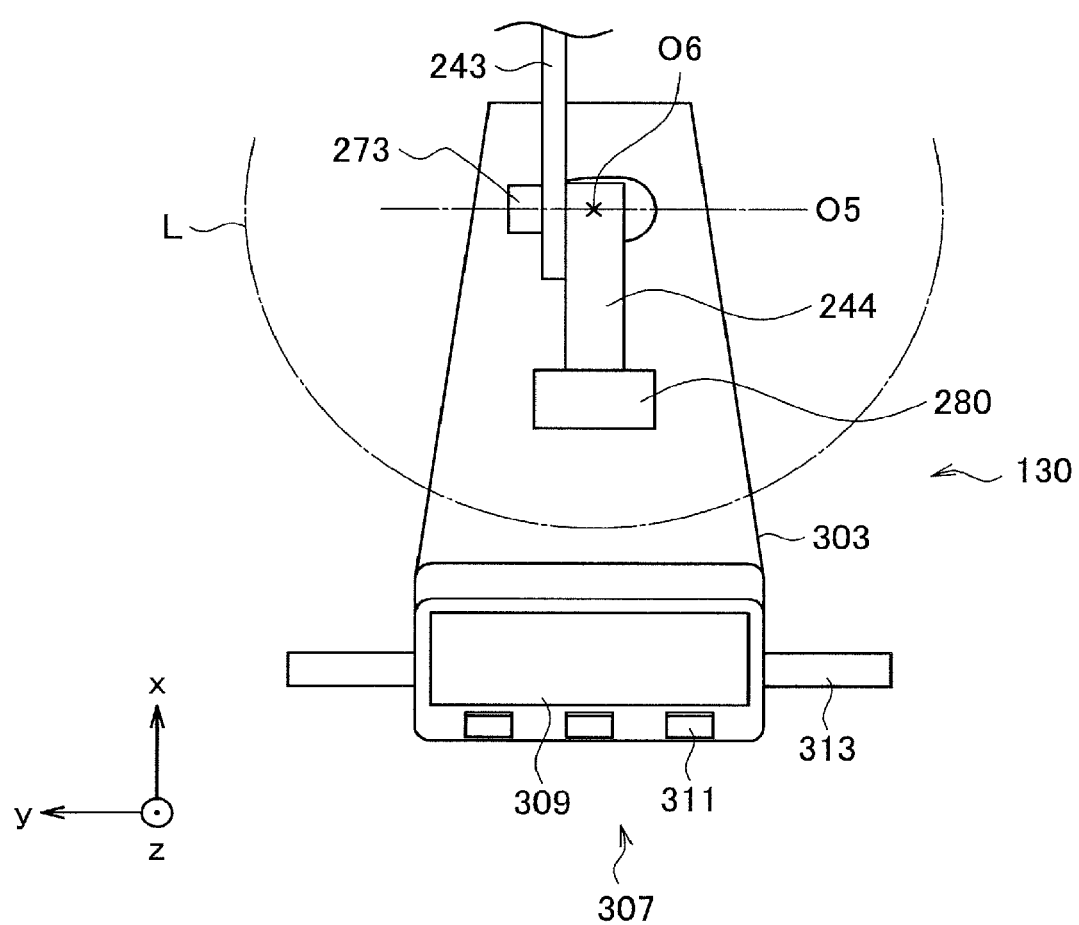
FIG. 3 is a diagram illustrating an example of a shape of a case body that forms a base section provided in the observation device according to the first embodiment.

Note that the shape of the case body 303 that forms the base section 130 is not limited to the examples illustrated in FIGS. 1 and 2. FIG. 3 is a diagram illustrating an example of the shape of the case body 303 that forms the base section 130 provided in the observation device 10 according to the first embodiment. FIG. 3 schematically illustrates a state in which the vicinity of the base section 130 is viewed from the upper side similarly to FIG. 2. In FIG. 3, the movable range of the counterweight 280 is represented by the symbol L similarly to FIG. 2.

As illustrated in FIG. 3, the case body 303 may have "a thinner shape on the front side (the positive side of the x axis illustrated in FIG. 3) of the case body 303 than on the rear side (the negative side of the x axis illustrated in FIG. 3) of the case body 303". As described above, since the case body 303 has a portion with the wall shape on the rear side, it is possible to arrange, inside the case body 303, a larger number of parts on the rear side of the case body 303 than on the front side (the positive side of the x axis illustrated in FIG. 1) of the case body 303. Therefore, the observation device according to the embodiment can employ the shape of the case body 303 as illustrated in FIG. 3.

The control section 305 has a processor such as a central processing unit (CPU) or a digital signal processor (DSP), a control substrate on which both such a processor and a storage element such as a memory are mounted, or the like, formed therein for example. The respective functions of the control section 305 are realized by the processor that forms the control section 305 executing arithmetic processing in accordance with a predetermined program. Note that an exhaust outlet 317 is provided in the case body 303 in order to circulate air related to air cooling of an element that generates heat, such as a processor that forms the control section 305. In the embodiment, the exhaust outlet 317 is provided in a surface in which the operation section 307 of the case body 303 is provided as illustrated in the drawings. However, the position of the exhaust outlet 317 is not limited to such an example, and the exhaust outlet 317 may be provided at an arbitrary position on the case body 303.

The control section 305 has a function of switching operation modes of the aforementioned holding section 120 by controlling driving of a brake that is provided in each rotational axis section of the holding section 120 in response to operating input of the surgeon via the aforementioned operation mode changing SW 153. Also, the control section 305 has a function of appropriately causing the optical system of the imaging section 111 of the microscope section 110 to drive in response to operating input of the surgeon via the aforementioned zoom SW 151 and the focus SW 152 and adjusting the magnitude and the focal distance of the microscope section 110. In addition, the control section 305 has a function of changing various kinds of setting or the like related to imaging performed by the microscope section 110, which will be described later, in response to operating input via the operation section 307.

In addition, the control section 305 performs various kinds of image processing such as gamma correction processing, white balance adjustment processing, enlargement processing related to an electronic zoom function, and interpixel correction processing, for example, on the image signal transmitted from the imaging section 111 of the microscope section 110. As the image processing, various kinds of image processing that is typically performed in order to display an image on the display device 20 may be performed. The control section 305 transmits the image signal on which the various kinds of image processing have been performed to the display device 20 and causes the display device 20 to display the image captured by the imaging section 111. Note that communication between the control section 305 and the display device 20 may be realized by various known wired or wireless schemes.

The operation section 307 has various input devices formed therein. In the example illustrated in the drawing, the operation section 307 has with a touch panel 309, various switches 311, a grip 313 that is gripped when the observation device 10 is caused to move, and a caster locking lever 315 that locks rotation of the casters 301 formed therein. Among them, it is possible to state that the grip 313 and the caster locking lever 315 are input devices related to an operation of moving the observation device 10. Hereinafter, the operation section that includes the input devices related to the operation of moving the observation device 10, such as the grip 313 and the caster locking lever 315, in the operation section 307 will also be referred to as an operation section related to the moving operation for distinguishing them as needed.

Here, since the movement itself of the observation device 10 is performed in a stage of setup before surgery (in this specification, this means a series of processing of placing the observation device 10 near the surgical bed and adjusting the position and the attitude of the microscope section 110 such that the surgical site is imaged in a desired direction and at a desired image angle), operating input to the operation section related to the moving operation is not typically performed during surgery. Meanwhile, various kinds of operating input can be performed during surgery from the aforementioned touch panel 309 and switches 311. Hereinafter, the operation section that includes input devices capable of receiving various kinds of operating input performed during surgery, such as the touch panel 309 and the switches 311, in the operation section 307 will also be referred to as an operation section related to operations during surgery for distinguishing them as needed.

During surgery, an assistant who is an operator, for example, performs various kinds of operating input via the operation section related to operations during surgery in response to oral instructions from the surgeon. For example, the assistant can change various kinds of setting related to imaging performed by the microscope section 110 via the touch panel 309 and the switches 311. Here, various kinds of setting related to the imaging performed by the microscope section 110 include, for example, a zoom speed (that is, a rate of change in the magnitude when the aforementioned zoom SW 151 is operated) in the microscope section 110, a focus speed (that is, a rate of change in the focal distance when the aforementioned focus SW 152 is operated) in the microscope section 110, ON/OFF switching of an AF function, changing of the magnitude of the electronic zoom, changing of the light amount of illumination light, changing of the type of the illumination light (for example, switching between white light for ordinary observation and narrow band light (such as infrared light) for special observation, changing of sensitivity, changing of diaphragm, changing of depth, and the like. In addition, the assistant, for example, can perform setting of image quality (for example, white balance, brightness, a color tone, and the like) in the display device 20, switching of display on the display device 20 (for example, switching between display in which only the image captured by the imaging section 111 is displayed on the display screen of the display device 20 and picture-in-picture (PIP) display and the like), and various operations on the display device 20.

Note that the operating input listed herein is just an example, and operating input for other matters may be performed using the operation section related to operations during surgery. It is possible to input various matters, the operating input of which can be performed via the operation section during surgery using an existing typical observation device, through the operation section related to operations during surgery. Also, the types of the input devices that form the operation section related to operations during surgery are not limited to the touch panel 309 and the switches 311, and the operation section related to operations during surgery may be formed by various known input devices.

The configurations of the observation system 1 according to the embodiment and the observation device 10 according to the first embodiment have been described above with reference to FIG. 1.

Note that the configuration of the observation device according to the embodiment is not limited to the observation device 10 illustrated with reference to FIG. 1.

Figure 4:
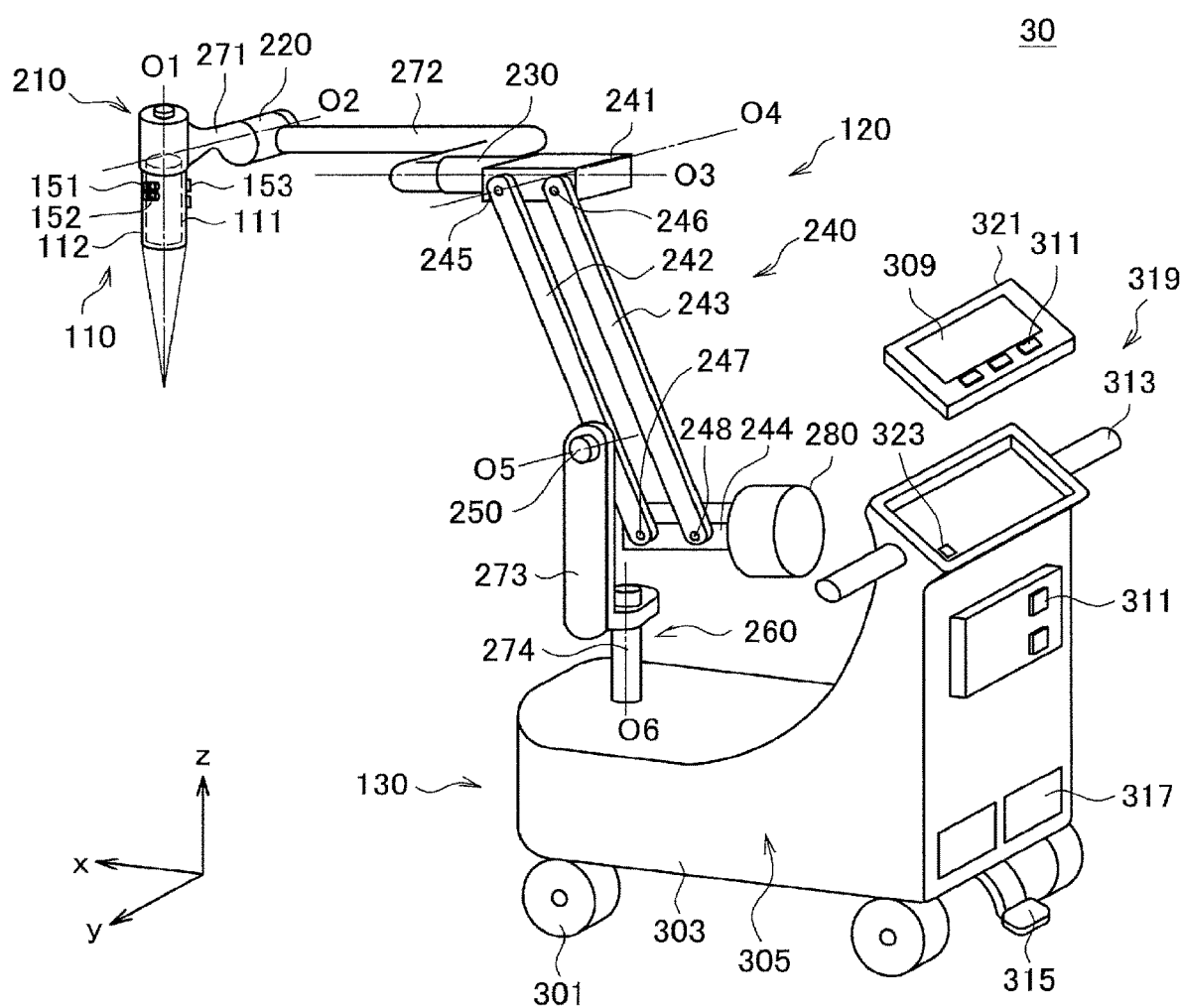
FIG. 4 is a diagram schematically illustrating a configuration example of an observation device according to a second embodiment.

FIG. 4 is a diagram schematically illustrating a configuration example of the observation device 30 according to the second embodiment. The observation device 30 is a medical observation device for observing a site to be observed similarly to the observation device 10 according to the first embodiment illustrated in FIG. 1.

The observation device 30 has a configuration (including configurations according to modification examples of the observation device 10) that is basically similarly to that of the observation device 10 according to the first embodiment illustrated in FIG. 1. A difference between the observation device 30 and the observation device 10 illustrated in FIG. 1 is an operation section 319 that forms the observation device 30.

The operation section 319 is formed with various input devices. A main difference between the operation section 319 and the operation section 307 that forms the observation device 10 illustrated in FIG. 1 is a point that the operation section 319 includes an operation device 321 that can be attached to and detached from the case body 303.

The operation device 321 has the touch panel 309 and various switches 311, for example. In addition, the operation device 321 includes a communication device (not illustrated) that performs communication (one of or both wired communication and wireless communication) with an external device such as a processor that forms the control section 305 provided inside the case body 303, for example. As the communication devices (not illustrated) provided in the operation device 321, devices that are compatible with an arbitrary communication scheme that enables wireless communication and an arbitrary communication scheme that enables wireless communication are listed, for example.

In a case in which the operation device 321 is attached to the case body 303, the operation device 321 is connected, in a wired manner, to the control section 305 that is provided in the case body 303 via a connection connector 323 provided in the case body 303. A role that the operation device 321 plays in a case in which the operation device 321 is attached to the case body 303 is similar to those of the touch panel 309 and various switches 311 that the operation section 307 illustrated in FIG. 1 has.

Note that in a case in which the operation device 321 is attached to the case body 303, the operation device 321 may be connected, in a wireless manner, to the control section 305 provided in the case body 303. In a case in which the operation device 321 and the control section 305 perform wireless communication when the operation device 321 is attached to the case body 303, the connection connector 323 may not be provided in the case body 303.

In addition, in a case in which the operation device 321 is detached from the case body 303, the operation device 321 is connected, in a wireless manner, to the control section 305 provided in the case body 303. In the case in which the operation device 321 is detached from the case body 303, the operation device 321 plays a role as a remote controller with which operations on the observation device 30 or the like can be performed.

The observation device 30 according to the second embodiment has a configuration illustrated in FIG. 4, for example.

Here, the observation device 30 has a configuration that is basically similar to that of the observation device 10 according to the first embodiment illustrated in FIG. 1.

Therefore, advantages that are similar to the advantages that are achieved in the case in which the observation device 10 according to the first embodiment is used are achieved using the observation device 30.

In addition, it is easy to attach and detach the operation device 321 during surgery by the detachable operation device 321 being provided on the rear side (the negative side of the x axis illustrated in FIG. 4) of the case body 303 in the observation device 30. Further, it is possible for the operator to perform operations on the observation device 30 or the like using the operation device 321 detached from the case body 303 and to thereby perform operations on the observation device 30 or the like without being restricted by arrangement of the observation device 30 during surgery.

Therefore, it is possible to further improve convenience of the operator in a case in which the observation device 30 is used.

Figure 5:
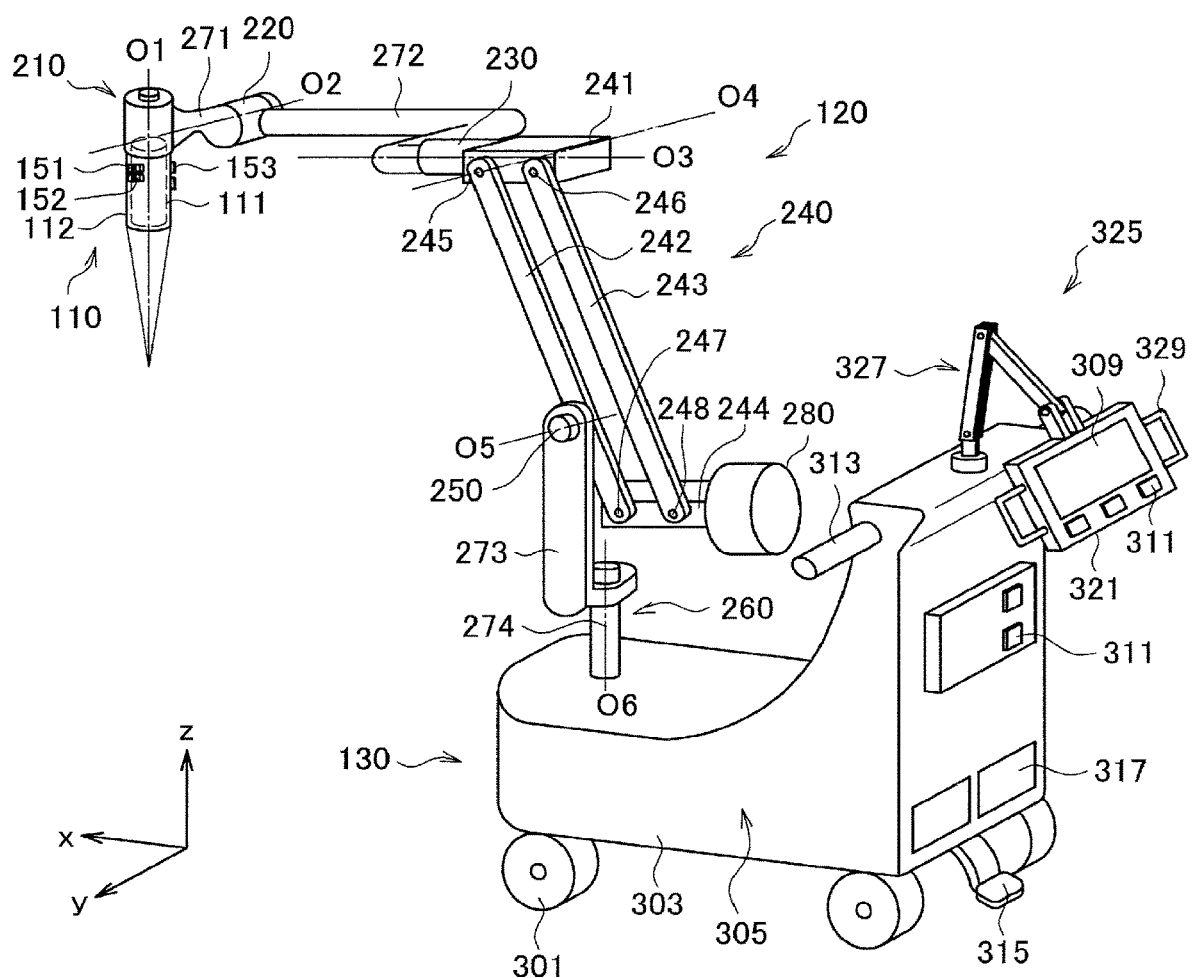
FIG. 5 is a diagram schematically illustrating a configuration example of an observation device according to a third embodiment.

FIG. 5 is a diagram schematically illustrating a configuration example of an observation device 40 according to a third embodiment. The observation device 40 is a medical observation device for observing a site to be observed similarly to the observation device 10 according to the first embodiment illustrated in FIG. 1.

The observation device 40 has a configuration (including configurations according to modification examples of the observation device 10) that is basically similar to that of the observation device 10 according to the first embodiment illustrated in FIG. 1. A difference between the observation device 40 and the observation device 10 illustrated in FIG. 1 is an operation section 325 that forms the observation device 40.

The operation section 325 is formed with various input devices. A main difference between the operation section 325 and the operation section 307 that forms the observation device 10 illustrated in FIG. 1 is a point that the operation section 325 includes the operation device 321 and a movable section 327.

The operation device 321 has the touch panel 309 and the various switches 311, for example. Also, the operation device 321 includes a communication device (not illustrated) for performing communication with an external device such as a processor that forms the control section 305 provided in the case body 303, for example, similarly to the operation device 321 according to the second embodiment illustrated in FIG. 4.

In addition, a handle 329 is provided in the operation device 321. It is possible for the operator to more easily change the position of the operation device 321 by the handle 329 being provided in the operation device 321. Here, the position of the operation device 321 is a three-dimensional spatial position in a space in which the observation device 40 is arranged, for example. Note that it is needless to say that the handle 329 may not be provided in the operation device 321.

The movable section 327 has one end connected to the case body 303 and the other end connected to the operation device 321. The movable section 327 supports the operation device 321 such that the position of the operation device 321 can be changed.

Figure 6:
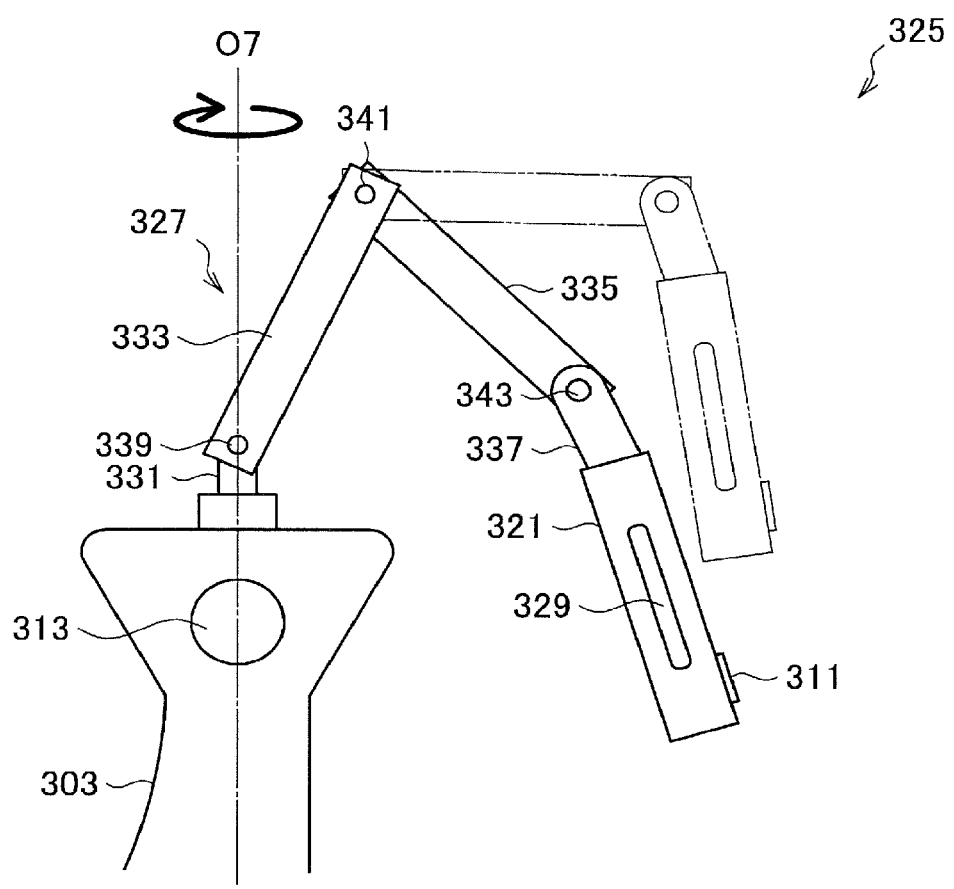
FIG. 6 is a diagram illustrating an example of a configuration of an operation section provided in the observation device according to the third embodiment.

FIG. 6 is a diagram illustrating an example of a configuration of the operation section 325 provided in the observation device 40 according to the third embodiment and illustrates a part of the configuration of the operation section 325 that includes the movable section 327 capable of changing the position of the operation device 321.

The movable section 327 has arms 331, 333, 335, and 337 and joint sections 339, 341, and 343.

The arm 331 has one end connected to the case body 303 and rotates about a rotational axis O7. In addition, the arm 333 is connected to the other end of the arm 331 such that the arm 333 can turn by the joint section 339. The rotational axis O7 is a rotational axis in the vertical direction relative to the case body 303. It is possible to change the orientation of the operation device 321 to orientation about the rotational axis O7 by the arm 331 turning about the rotational axis O7. Here, the orientation of the operation device 321 is an orientation that is arbitrarily defined relative to the operation device 321, such as a vertical direction of the touch panel 309 that the operation device 321 has, for example.

The arm 331 is connected to one end of the arm 333 such that the arm 331 can turn by the joint section 339, and the arm 335 is connected to the other end of the arm 333 such that the arm 335 can turn by the joint section 341.

The arm 333 is connected to one end of the arm 335 such that the arm 333 can turn by the joint section 341, and the arm 337 is connected to the other end of the arm 335 such that the arm 337 can turn by the joint section 343.

The arm 335 is connected to one end of the arm 337 such that the arm 335 can turn by the joint section 343, and the operation device 321 is connected to the other end of the arm 337.

The operator can freely change the position and the orientation of the operation device 321 by the movable section 327 having the configuration illustrated in FIG. 6.

Note that the configuration of the operation section 325 provided in the observation device 40 according to the third embodiment is not limited to the example described with reference to FIG. 6. For example, the movable section that forms the operation section 325 may not include the configuration that turns about the rotational axis O7.

The observation device 40 according to the third embodiment has the configurations illustrated in FIGS. 5 and 6, for example.

Here, the observation device 40 has a configuration that is basically similar to that of the observation device 10 according to the first embodiment illustrated in FIG. 1.

Therefore, advantages that are similar to the advantages that are achieved in the case in which the observation device 10 according to the first embodiment is used are achieved using the observation device 40.

In addition, since the position of the operation device 321 can be changed by the movable section 327 in the observation device 40, it is possible for the operator to freely change the position and the orientation of the operation device 321. Further, since the operation device 321 is provided on the rear side of the case body 303 (the negative side of the x axis illustrated in FIG. 5), it is easy to change the position and the orientation of the operation device 321 during surgery.

Therefore, it is possible to further improve convenience of the operator in a case in which the observation device 40 is used.

2. Advantages of Observation Device

Actions that are achieved by the observation device according to the embodiment as described above will be described in detail by exemplifying the observation device 10 according to the first embodiment. Note that as described above, the observation device 30 according to the second embodiment and the observation device 40 according to the third embodiment have configurations that are basically similar to the configuration of the observation device 10 according to the first embodiment. Therefore, actions that are achieved by the observation device 30 and the observation device 40 are similar to those of the observation device 10.

As described above, the operation section 307 is provided at the base section 130 in the observation device 10 in the embodiment.

Here, configurations corresponding to the control section 305 and the operation section 307 according to the embodiment are provided as a part of the holding section in an existing typical observation device as illustrated in Non-Patent Literatures 1 and 2. Specifically, both the holding sections of the observation devices described in Non-Patent Literatures 1 and 2 are configured as balance arms that have six rotational axes corresponding to six degrees of freedom, and the control section and the operation section are integrally provided with the link provided between the sixth axis O6 located furthest on the base end side and the fifth axis O5 that is provided next to the sixth axis. In association with the configuration illustrated in FIG. 1, the configurations of the observation device described in Non-Patent Literatures 1 and 2 correspond to a configuration in which the control section and the operation section are provided at the third arm section 273. Note that with such a configuration, there is an advantageous effect that it is possible to form the device that is relatively small as an optical type microscope device as described above.

However, with such a configuration, the control section and the operation section also rotate with the holding section together in a case in which the holding section rotates about the sixth axis O6. That is, if the setting of the observation is performed and the position and the attitude of the microscope section are decided, the attitude of the holding section is decided in accordance with the position and the attitude, and the positions and the orientations of the control section and the operation section are also automatically decided. That is, the existing observation device has a property that a degree of freedom in arrangement of the control section and the operation section during surgery is low. Such a property may be a factor that prevents surgery from being smoothly executed.

For example, although a cable for supplying power may extend outward from the control section, there is a concern that the cable prevents movement of members of medical staff in the operating room and arrangement of the device depending on the extending direction. Meanwhile, since the position and the orientation of the control section are uniquely decided in the existing observation device, the extending direction of such a cable from the control section is also uniquely decided. Therefore, there may be a disadvantage that even if the cable prevents surgery from being smoothly executed as a result of setting the observation device, it is not possible to freely change the position thereof in the existing configuration.

In addition, it is preferable that the operator be able to visually recognize the display screen of the display device 20 in order to check how surgery is going on and be located at a position at which the operator can visually recognize the surgeon on order to clearly receive instructions from the surgeons during surgery for smooth execution of the surgery, for example. However, since the position and the orientation of the operation section are uniquely decided in the existing observation device, the position of the operator during surgery is uniquely decided. Therefore, there may be a disadvantage that even if the operator cannot be positioned at a preferable location as described above as a result of setting the observation device, the operator cannot freely change the position with the existing configuration.

In addition, an exhaust outlet (corresponding to the exhaust outlet 317 in the embodiment) for circulating air when the processor or the like is cooled with air can be provided in the control section, for example, and the position and the orientation of the exhaust outlet are preferably adjusted such that the exhaust air is not directed to the patient. However, since the position and the orientation of the control section are uniquely decided in the existing observation device, the position and the orientation of the exhaust outlet are also uniquely decided. Therefore, there may be a disadvantage that even if the exhaust outlet is directed to the patient as a result of setting the observation device, the position and the direction of the exhaust outlet cannot be freely changed in the existing configuration.

In this manner, the degree of freedom in the arrangement of the control section, the operation section, and the exhaust outlet are low in the existing typical observation device. Therefore, there is a probability that in a case in which the position and the orientation of the control section, the operation section, and/or the exhaust outlet are disadvantageous when the observation device is set once, it is necessary to change the position of the observation device relative to the surgical bed and to search for a position at which such a disadvantage does not occur. In this case, there is a probability that smooth surgery is inhibited since there may be a concern that an operation of repeating the setting occurs.

Meanwhile, according to the observation device 10 in the embodiment, the control section 305, the operation section 307, and the exhaust outlet 317 are provided in the base section 130. That is, the control section 305, the operation section 307, and the exhaust outlet 317 are provided as configurations that are separate from the holding section 120. With such a configuration, the position and the attitude of the microscope section 110 are decided for observation, and even if the attitude of the holding section 120 is decided in accordance with the position and the attitude, it is possible to change the position and the orientation of the base section 130 within a range in which the position and the attitude of the microscope section 110 are not changed. Therefore, the positions and the orientations of the control section 305, the operation section 307, and the exhaust outlet 317 can also freely be changed within the range.

Figure 7:
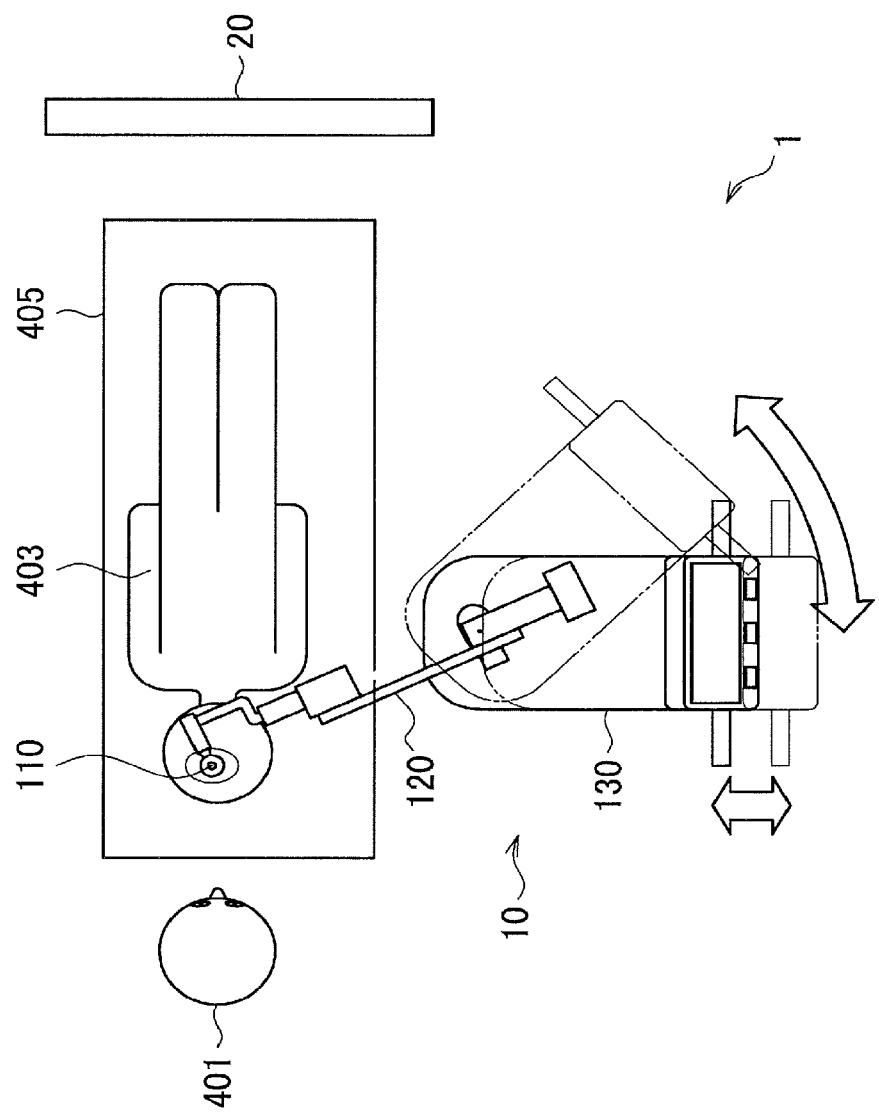
FIG. 7 is a diagram for describing movement of the base section in a state in which the position and the attitude of a microscope section are fixed.

FIG. 7 is a diagram for describing movement of the base section 130 in a state in which the position and the attitude of the microscope section 110 are fixed. FIG. 7 schematically illustrates an example of positional relationships of a surgeon 401, a patient 403 on the surgical bed 405, the display device 20, and the observation device 10 in surgery to which the observation system 1 according to the embodiment is applied. FIG. 7 illustrates an example of arrangement thereof in a stage in which setting has been completed. As illustrated in the drawing, the display device 20 is mounted on the opposite side of the surgeon 401 with the surgical bed 405 interposed therebetween. In addition, the observation device 10 is mounted on the side of a side surface of the surgical bed 405. The holding section 120 extends from the observation device 10, and the position and the attitude of the microscope section 110 are adjusted above the surgical site such that a surgical site (a head portion in the example illustrated in the drawing) of the patient 403 can be imaged.

As illustrated in FIG. 7, it is possible to change the position and the orientation of the base section 130 about the sixth axis O6 while fixing the position and the attitude of a configuration on the tip end side beyond the holding section 120, that is, the microscope section 110 by rotating the base section 130 about the sixth axis O6 in such a state according to the observation device 10. Also, it is possible to cause the base section 130 to move in the front-back direction while fixing the position and the attitude of the microscope section 110 by appropriately adjusting rotation at the respective rotational axes between the sixth axis O6 of the holding section 120 and the microscope section 110.

In this manner, it is possible to change the positions and the orientations of the control section 305, the operation section 307, and the like while fixing the position and the attitude of the microscope section 110 after the setting is completed, by providing the control section 305, the operation section 307, and the like in the base section 130 rather than the holding section 120 in the embodiment. Therefore, in a case in which the position and the orientation of the control section 305, the operation section 307, and/or the exhaust outlet 317 are disadvantageous as a result of setting the observation device 10, for example, it is possible to move only the base section 130 while fixing the position and the attitude of the microscope section 110, thereby appropriately adjusting the positions and the orientations of the control section 305, the operation section 307, and the exhaust outlet 317 such that the disadvantage is solved. Therefore, surgery can more smoothly be executed.

Further, according to the observation device 10, the following advantages can also be achieved.

Typically, there are concepts of a clean area and an unclean area for surgical operations, and presence of objects and persons that belong to the unclean area in the clean area has to be avoided. The top of the surgical bed 405 is the clean area, and the surgeon 401 also belongs to the clean area during surgery. Also, the holding section 120 and the microscope section 110 of the observation device 10 that may be arranged near the patient 403 are covered with a sterilized drape.

Meanwhile, the base section 130 of the observation device 10 belongs to the unclean area. Therefore, in a case in which it is desired to change various kinds of setting during surgery, it is not possible for the surgeon 401 himself/herself to perform operating input via the operation section 307. Therefore, the assistant serves as an operator and performs operating input from the operation section 307 in response to oral instructions from the surgeon 401.

Here, the observation device 10 according to the embodiment is an electronic imaging type observation device and can be formed to be smaller than an optical observation device as described above. Therefore, the observation device 10 is used by being mounted at a position that is closer to the surgical bed 405 than in the optical type observation device. Therefore, the operation section 307 that belongs to the unclean area and the operator thereof can be located at a position closer to the surgical bed 405, that is, closer to the clean area. In a case in which the operation section 307 is located near the clean area, there is a concern that it becomes difficult to smoothly perform operating input since it is necessary for the operator to perform the operating input via the operation section 307 while keeping out from the clean area.

Here, a case in which the configurations of the optical type observation devices described in Non-Patent Literatures 1 and 2 are applied to the electronic imaging type observation device will be examined. In this case, the base end of the holding section is connected to the approximate center of the plate-shaped base section with the upper surface with a substantially square shape in the configurations described in Non-Patent Literatures 1 and 2. In addition, the operation section is provided as a part of the holding section. Therefore, the operation section is located at a position closer to the clean area by the observation device, that is, the base section being mounted at a position closer to the surgical bed 405. In addition, since a degree of freedom related to arrangement of the operation section is low in such a configuration as described above, it is not possible to cause the operation section to move such that the operation section is kept away from the clean area even a little bit in a case in which the operation section is located near the clean area in this manner, and it is not possible to suitably avoid difficulty in performing the aforementioned operating input. In this manner, it is possible to state that typical arrangement of the operation section in the optical type observation device is not necessarily appropriate as arrangement of the operation section in the electronic imaging type observation device in terms of a positional relationship between the clean area and the operation section.

Meanwhile, according to the observation device 10 in the embodiment, the operation section 307 is provided in the base section 130 rather than the holding section 120 as described above. Also, at this time, the operation section 307 is provided on a side opposite to the side on which the holding section 120 is provided with the approximate center in the horizontal plane of the upper surface of the base section 130. That is, since the operation section 307 is arranged at a relatively far position from the holding section 120, it is possible to keep the operation section 307 away from the clean area. Further, by the shape of the upper surface of the base section 130 having the long-side direction and the short-side direction, arranging the holding section 120 on one end side in the long-side direction, and arranging the operation section 307 on the other end side as in the aforementioned configuration example at this time, it is possible to keep both the holding section 120 and the operation section 307 further away from each other at longer distance. In this manner, since the operation section 307 and the surgical bed 405 located in a direction in which the holding section 120 extends are kept further away from each other at a longer distance even if the observation device 10, that is, the base section 130 is arranged near the surgical bed 405, risk that the operator enters the clean area decreases. Therefore, smoother surgery can be realized.

Further, it is possible to move only the base section 130 while fixing the position and the attitude of the microscope section 110 and to adjust the position and the orientation of the operation section 307 in the observation device 10. Therefore, it is possible to adjust the position and the orientation of the operation section 307 such that the operation section 307 is kept away from the clean area as much as possible in a case in which the operation section 307 has come closer to the clean area as a result of setting regardless of contriving of the arrangement of the holding section 120 and the operation section 307 as described above. In this manner, a risk that the operator enters the clean area can be further suitably reduced.

In this manner, the observation device 10 according to the embodiment can suitably solve a disadvantage that may occur because of the electronic imaging type observation device due to a property that the observation device can be mounted at a position closer to the surgical bed 405, this is not problematic in the optical type observation device. That is, it is possible to state that the observation device 10 can provide arrangement of the operation section 307 that is appropriate for the electronic imaging type observation device.

3. Operations During Use

Operations during use of the observation device 10 according to the embodiment will be described. First, the holding section 120 is covered with a sterilized drape in order to secure cleanliness of the holding section 120 as preparation before use (before surgery).

Next, a member of medical staff who belongs to an unclean area grips the grip 313, uses the caster 301, and causes the observation device 10 to move near the surgical bed 405.

Next, the surgeon 401 grips the grip section of the microscope section 110 through the sterilized drape, presses the operation mode changing SW 153 to set an operation mode of the holding section 120 to a free mode (that is, while brakes provided from the first axis O1 to the sixth axis O6 is released), and adjusts the position and the attitude of the microscope section 110 such that the surgical site can be imaged in a desired direction and at a desired image angle.

At this time, the surgeon 401 continuously presses the operation mode changing SW 153 even after finishing positioning of the microscope section 110. Then, the member of medical staff who grips the grip 313 adjusts the position and the direction of the operation section 307 at a position at which the operator can easily perform operating input while the operation mode changing SW 153 is being pressed.

For example, the member of medical staff can adjust the orientation of the operation section 307 by causing the base section 130 to rotate about the sixth axis O6 as illustrated in FIG. 7. In this case, since the attitude of the holding section 120 does not change, the position and the orientation of the operation section 307 are adjusted while the position and the attitude of the microscope section 110 are maintained. In addition, the member of medical staff can adjust the position of the operation section 307 by causing the base section 130 in the front-back direction as similarly illustrated in FIG. 7, for example. In this case, since the position and the attitude of the microscope section 110 are fixed by the surgeon 401, the configuration between the sixth axis O6 of the holding section 120 and the microscope section 110 is deformed, and the orientation of the operation section 307 is adjusted while the position and the attitude of the microscope section 110 are maintained, by the member of medical staff causing the base section 130 to move in the front-back direction.

If the adjustment of the position and the orientation of the operation section 307 finishes, the surgeon 401 releases the operation mode changing SW 153 and changes the operation mode of the holding section 120 to a locked mode (that is, the brakes provided from the first axis O1 to the sixth axis O6 are caused to work). In addition, the member of medical staff who grips the grip 313 presses the caster locking lever 315, locks the casters 301, and fixes the position of the observation device 10. Note that although the case in which the position and the orientation of the operation section 307 are adjusted in consideration of convenience of the operator has been described here as an example, orientations of a cable for supplying power that extends from the control section 305 to the outside, the exhaust outlet 317, and the like, for example, may be adjusted together such that the cable, the exhaust outlet 317, and the like are in such appropriate arrangement that the aforementioned disadvantage does not occur.

The surgeon 401 starts surgery while referring to the display device 20. The assistant who is the operator is located in front of the operation section 307 and performs operations such as changing of setting via the touch panel 309 and the various switches 311 in response to instructions from the surgeon 401 or in accordance with conditions of the surgery.

4. Other Configuration Examples of Observation Device

The aforementioned configuration of the observation device 10 is just an example, and the observation device 10 according to the embodiment may have another configuration. In the observation device 10 according to the embodiment, it is only necessary to provide at least the operation section 307 in the base section 130 rather than the holding section 120, and the other configurations may be arbitrarily employed. It is possible to change the position and the orientation of the operation section 307 while fixing the position and the attitude of the microscope section 110 as described above by having the configuration in which the operation section 307 is provided in the base section 130, and it is thus possible to obtain an effect that smoother surgery is realized.

For example, the configuration of the holding section 120 may be arbitrarily employed in the embodiment. For example, the holding section 120 may not be configured as a balance arm. Also, the number and the arrangement of the rotational axis sections that form the holding section 120 may be arbitrarily employed.

In addition, a connection position of the holding section 120 relative to the base section 130 may also arbitrarily be employed. Although in the aforementioned configuration example, the base end of the holding section 120 is connected to the position deviating from the approximate center in the horizontal plane of the upper surface of the base section 130 toward the front side, for example, the embodiment is not limited to such an example. The base end of the holding section 120 may be connected to the approximate center in the horizontal plane of the upper surface of the base section 130. However, it is possible to obtain the effect that the operation section 307 is kept further away from the clean area by locating the connection position of the base end of the holding section 120 at the position deviating from the approximate center in the horizontal plane of the upper surface of the base section 130 toward the front side as in the aforementioned configuration example and arranging the operation section 307 on the opposite side thereof.

In addition, the shape of the base section 130 is also not limited to the aforementioned configuration example. For example, although the shape of the upper surface of the base section 130 has a long-side direction and the short-side direction in the aforementioned configuration example, the embodiment is not limited to such an example. The base section 130 may be formed such that the shape of the upper surface thereof has a substantially square shape or a circular shape. However, it is possible to obtain the effect that the operation section 307 is kept further away from the clean area by forming the base section 130 such that the shape of the upper surface has the long-side direction and the short-side direction and arranging the holding section 120 and the operation section 307 on the one end side and the other end side of the long-side direction, respectively, as in the aforementioned configuration example.

In addition, the arrangement of the operation section 307 in the base section 130 may arbitrarily be employed. Although the respective input devices that form the operation section 307 are provided such that the input devices concentrate on the rear side of the base section 130 in the aforementioned configuration example, for example, the embodiment is not limited to such an example. The respective input devices that form the operation section 307 may be provided at arbitrary positions in the base section 130. However, arrangement of these input devices is preferably decided in consideration of operability of the operator. For example, the input device that the operator can manually operate, such as the touch panel 309 and the switches 311, may be arranged at heights at which the operator can easily manually operate the input devices from a viewpoint of human engineering. Also, it is possible to obtain the effect that the operation section 307 is kept further away from the clean area by arranging the holding section 120 on the tip end side of the base section 130 and arranging the operation section on the rear side of the base section 130 as in the aforementioned configuration example.

In addition, an actuator that drives and rotates the rotational axis section may be provided for at least any of the rotational axis sections of the holding section 120. In this case, the control section 305 can further have a function of controlling operations of the holding section 120 by causing such an actuator to drive. In this case, various known control schemes such as position control or force control may be used as a control scheme when the control section 305 controls operations of the holding section 120. In addition, operating input of the holding section 120 using a so-called navigation function may be performed via the operation section 307 in this case. With the navigation function, the control section 305 can cause the holding section 120 to operate and causes the microscope section 110 to automatically move such that a site designated on the display screen on which the image captured by the microscope section 110 is displayed is located at the center of the image angle. For example, the control section 305 may cause the microscope section 110 to move such that the surgical site imaged by the microscope section 110 is displayed on the display screen of the touch panel 309 that forms the operation section 307 and the site designated by the operator on such a touch panel 309 is located at the center of the image angle with such a navigation function.

In addition, in a case in which the actuator is provided for each rotational axis section of the holding section 120, the observation device 10 may be configured as a so-called robot device that autonomously operates on the basis of a predetermined algorithm. In this case, various kinds of setting (for example, selection of algorithms for operations of the holding section 120 in accordance with a surgical procedure, switching of a moving speed of the holding section 120) related to such autonomous operations may be performed via the operation section 307.

5. Supplement

The preferred embodiments of the present disclosure have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A medical observation device including:
a microscope section that images a surgical site;
a holding section that holds the microscope section on a tip end side;
a base section to which a base end of the holding section is connected; and
an operation section that is provided at the base section for performing various kinds of operating input.

(2)

The medical observation device according to (1),
in which the holding section is configured as a balance arm provided with a counterweight, and
the operation section is arranged outside a movable range of the counterweight.

(3)

The medical observation device according to (1) or (2), in which a rotational axis section that has a rotational axis in a vertical direction relative to the base section is arranged at the base end of the holding section that is connected to an upper surface of the base section.

(4)

The medical observation device according to any one of (1) to (3), in which the base end of the holding section is connected to a front side beyond an approximate center in a horizontal plane of the base section on the upper surface of the base section.

(5)

The medical observation device according to any one of (1) to (4), in which the operation section is arranged on a rear side beyond the approximate center in the horizontal plane of the base section.

(6)

The medical observation device according to any one of (1) to (5),
in which a shape of the upper surface of the base section has a long-side direction and a short-side direction, and
the base end of the holding section is provided on one end side in the long-side direction beyond the approximate center in the horizontal plane of the base section while the operation section is provided on the other end side in the long-side direction beyond the approximate center in the horizontal plane of the base section.

(7)

The medical observation device according to any one of (4) to (6), in which at the base section, a caster that is able to move on a contact surface is provided on each of a front side beyond a position to which the base end of the holding section is connected in the horizontal plane of the base section and a rear side beyond a position to which the base end of the holding section is connected in the horizontal plane of the base section.

(8)

The medical observation device according to any one of (1) to (7),
in which the base section has a portion with a substantially rectangular shape and a portion with a wall shape that is provided to protrude upward from a position corresponding to one side of an upper surface of the portion with the substantially rectangular shape, and
the operation section is provided on a wall surface that faces an outside of the portion with the wall shape.

(9)

The medical observation device according to any one of (1) to (8), in which the operation section includes an operation section for receiving operating input that is performed during surgery.

(10)

The medical observation device according to any one of (1) to (9), in which an input device that forms the operation section includes a touch panel and a switch.

(11)

The medical observation device according to any one of (1) to (10), in which the operation section includes an operation section for performing an operation of moving the observation device.

(12)

The medical observation device according to any one of (1) to (11), in which an input device that forms the operation section includes a grip that is gripped when the medical observation device is caused to move and a caster locking lever for locking rotation of a caster of the medical observation device.

(13)

The medical observation device according to any one of (1) to (12), in which the operation section includes an operation device that is attachable to and detachable from the base section.

(14)

The medical observation device according to any one of (1) to (12), in which the operation section includes
  an operation device, and
  a movable section that supports the operation device such that a position of the operation device is able to be changed.

(15)

A medical observation system including:
  a medical observation device that includes
    a microscope section that images a surgical site,
    a holding section that holds the microscope section on a tip end side,
    a base section to which a base end of the holding section is connected, and
    an operation section that is provided at the base section for performing various kinds of operating input; and
  a display device that displays an image captured by the medical observation device.

REFERENCE SIGNS LIST 1 observation system
10, 30, 40 observation device
20 display device
110 microscope section
111 imaging section
112 barrel section
120 holding section (arm section)
130 base section
151 zoom switch
152 focus switch
153 operation mode changing switch
210 first rotational axis section
220 second rotational axis section
230 third rotational axis section
240 fourth rotational axis section (parallelogram link mechanism)
241, 242, 243, 244, 331, 333, 335, 337 arm
245, 246, 247, 248, 339, 341, 343 joint section
250 fifth rotational axis section
260 sixth rotational axis section
271 first arm section
272 second arm section
273 third arm section
274 fourth arm section
280 counterweight
301 caster
303 case body
305 control section
307, 319, 325 operation section
309 touch panel
311 switch
313 grip
315 caster locking lever
317 exhaust outlet
321 operation device
323 connection connector
327 movable section
329 handle
401 surgeon
403 patient
405 surgical bed

The invention claimed is:

1. A medical observation device comprising:
  a microscope configured to image a surgical site;
  a holding section that holds the microscope on a tip end side;
  a base section to which a base end of the holding section is connected; and
  an operation section configured to receive operating input, the operation section being provided at the base section, wherein
  the holding section is configured as a balance arm provided with a counterweight,
  when the base section is viewed from an upper side of the medical observation device, the base section has a first area inside a movable range of the counterweight and a second area outside the movable range of the counterweight on an upper surface of the base section,
  the base end of the holding section is connected to the base section at a location in the first area on the upper surface of the base section, and
  the operation section is arranged at another location in the second area on the upper surface of the base section.

2. The medical observation device according to claim 1, wherein
  a rotational axis section that has a rotational axis in a vertical direction relative to the base section is arranged at the base end of the holding section that is connected to the upper surface of the base section.

3. The medical observation device according to claim 2, wherein
  the base end of the holding section is connected to a front side beyond an approximate center in a horizontal plane of the base section on the upper surface of the base section.

4. The medical observation device according to claim 3, wherein
  the operation section is arranged on a rear side beyond the approximate center in the horizontal plane of the base section.

5. The medical observation device according to claim 4, wherein
  a shape of the upper surface of the base section has a long-side direction and a short-side direction, and
  the base end of the holding section is provided on one end side in the long-side direction beyond the approximate center in the horizontal plane of the base section while the operation section is provided on the other end side in the long-side direction beyond the approximate center in the horizontal plane of the base section.

6. The medical observation device according to claim 3, wherein at the base section, a caster configured to move on a contact surface is provided on each of a front side beyond a position to which the base end of the holding section is connected in the horizontal plane of the base section and a rear side beyond a position to which the base end of the holding section is connected in the horizontal plane of the base section.

7. The medical observation device according to claim 1, wherein
the base section has a portion with a substantially rectangular shape and a portion with a wall shape that is provided to protrude upward from a position corresponding to one side of an upper surface of the portion with the substantially rectangular shape, and
the operation section is provided on a wall surface that faces an outside of the portion with the wall shape.

8. The medical observation device according to claim 1, wherein
the operation section is configured to receive the operating input that is performed during surgery.

9. The medical observation device according to claim 8, wherein
an input device that forms the operation section includes a touch panel and a switch.

10. The medical observation device according to claim 1, wherein
the operation section is configured to receive an input for moving the medical observation device.

11. The medical observation device according to claim 10, wherein
an input device that forms the operation section includes a grip that is gripped when the medical observation device is caused to move and a caster locking lever for locking rotation of a caster of the medical observation device.

12. The medical observation device according to claim 1, wherein
the operation section includes an operation device that is attachable to and detachable from the base section.

13. The medical observation device according to claim 1, wherein
the operation section includes
an operation device, and
a movable section that supports the operation device such that a position of the operation device is able to be changed.

14. A medical observation system comprising:
a medical observation device that includes
a microscope configured to image a surgical site,
a holding section that holds the microscope on a tip end side,
a base section to which a base end of the holding section is connected, and
an operation section configured to perform operating input, the operation section being provided at the base section; and
a display device that displays an image captured by the medical observation device, wherein
the holding section is configured as a balance arm provided with a counterweight,
when the base section is viewed from an upper side of the medical observation device, the base section has a first area inside a movable range of the counterweight and a second area outside the movable range of the counterweight on an upper surface of the base section,
the base end of the holding section is connected to the base section at a location in the first area on the upper surface of the base section, and
the operation section is arranged at another location in the second area on the upper surface of the base section.

* * * * *